US006372940B1

(12) United States Patent
Cavazza

(10) Patent No.: US 6,372,940 B1
(45) Date of Patent: Apr. 16, 2002

(54) PROCESS FOR THE PREPARATION OF NON-HYGROSCOPIC SALTS OF L(−)-CARNITINE

(75) Inventor: Claudio Cavazza, Rome (IT)

(73) Assignee: Sigma-Tau Industrie Farmaceutiche Riunite S.p.A, Rome (IT)

(*) Notice: Subject to any disclaimer, the term of this patent is extended or adjusted under 35 U.S.C. 154(b) by 0 days.

(21) Appl. No.: 09/868,980

(22) PCT Filed: Mar. 16, 2000

(86) PCT No.: PCT/EP00/02344

§ 371 Date: Jun. 22, 2001

§ 102(e) Date: Jun. 22, 2001

(87) PCT Pub. No.: WO00/56701

PCT Pub. Date: Sep. 28, 2000

(30) Foreign Application Priority Data

Mar. 19, 1999 (IT) .......................................... MI99A0551

(51) Int. Cl.$^7$ ........................ C07C 227/18; C07C 69/34; C07C 229/22
(52) U.S. Cl. ........................................ 562/553; 560/196
(58) Field of Search ........................... 562/553; 560/196

(56) References Cited

FOREIGN PATENT DOCUMENTS

| EP | 0 434 088 | 6/1991 |
| WO | WO98/38157 | 9/1998 |

*Primary Examiner*—Charanjit S. Aulakh
(74) *Attorney, Agent, or Firm*—Nixon & Vanderhye

(57) ABSTRACT

An improved process for the preparation of non-hygroscopic salts of L(−)-carnitine, in which the characterizing step comprises heating a mixture comprising L(−)-carnitine inner salt and a fumaric acid or tartaric acid.

6 Claims, No Drawings

PROCESS FOR THE PREPARATION OF NON-HYGROSCOPIC SALTS OF L(−)-CARNITINE

This application is a 371 of PCT IEP00/02349 filed Mar. 16,2000, now WO 00/56701.

The present invention relates to a process for the preparation of non-hygroscopic salts of L(−)-carnitine. More precisely, the present invention relates to an improved process for the preparation of L(−)-carnitine acid fumarate (1:1) and of L(−)-carnitine L(+)-tartrate (2:1) by "humid melting", as it will be further specified in the following.

The high hygroscopicity of L(−)-carnitine inner salt recognizedly causes complex problems of processability, stability and storage both of the raw materials and of the finished products. For example, L(−)-carnitine inner salt tablets have to be packaged in blisters to prevent contact with the air, since, otherwise, even in the presence of normal humidity conditions, they would undergo alterations, swelling up and becoming pasty and sticky. However, the solid orally administrable compositions are the preferred presentation form, inasmuch as they make it particularly easy for users to take the substances and comply with optimum dosage regimens.

Up to now, the problem of L(−)-carnitine inner salt hygroscopicity has been approached by transforming it into salts with pharmacologically acceptable acids, provided these salts have the same therapeutical/nutritional activities of the inner salt and do not have unwanted toxic or side effects.

There is now an extensive body of literature, particularly patents, disclosing the production of stable, non-hygroscopic salts of L(−)-carnitine.

U.S. Pat. No. 4,602,039 (Sigma-Tau) discloses L(−)-carnitine acid fumarate (1:1) as a non-hygroscopic, pharmacologically acceptable L(−)-carnitine salt. EP 0,434,088 (Lonza) discloses the use of L(−)-carnitine tartrate (2:1), the preparation and physico-chemical characterization of which were, on the other hand, described by D.Muller and E.Strack in Hoppe Seyler's Z.

Physiol. Chem. 353, 618–622, April 1972, for the preparation of solid forms suitable for the oral administration, such as tablets, capsules, powders or granulates, as said salts are capable of resisting at about 60% relative humidity.

The traditional processes for the industrial production of the two above mentioned salts (the only ones developed and marketed, up to now) have remarkable drawbacks in that they involve the use of large amounts of water or hydroalcoholic solutions in which L(−)-carnitine and the suitable acid are dissolved for carrying out the salification, and of organic solvents (such as methanol, ethanol and isobutanol) for the subsequent crystallization. For instance, according to the previously cited EP 0,434,088, L(−)-carnitine inner salt is added to a boiling solution of L(+)tartaric acid in aqueous 90% ethanol. This makes it necessary to concentrate large volumes of the solution containing the desired L(−)-carnitine at 50–60° C. and under reduced pressure (about 200 Torr, 26664 Pa) for carrying out the crystallization, with remarkable energy waste and no quantitative yield.

In order to drastically reduce said energy waste and to avoid the use of organic solvents, WO 98/38157 discloses a process in which L(−)-carnitine inner salt is mixed at room temperature with the minimum amount of water necessary to obtain a slurry of semiliquid/pasty consistency which is added, at room temperature, with an equimolar amount of fumaric acid or one-half the equimolar amount of L(+)-tartaric acid with respect to L(−)-carnitine inner salt (in L(−)-carnitine acid fumarate the L(−)-carnitine/fumarate molar ratio is 1:1, whereas in L(−)-carnitine tartrate the L(−)-carnitine/tartrate molar ratio is 2:1). The above pasty mixture (containing 10 to 30% by weight of water) is blended at room temperature with formation of a solid mass consisting of the desired salt (100% yield) which is subsequently ground to the wanted particle size.

However, the absence of hygroscopicity and a suitable particle size distribution are not yet sufficient to provide an excellent processability of said compounds on standard devices for the preparation of finished pharmaceutical forms, in that the above processes do not always provide reproducible, steady and optimum density values of the products. It is in fact known that an inadequately low density (for example, for L(−)-carnitine acid fumarate, a tapped density value below 0.7 g/mL) provides a too light and flaky product which involves serious processability problems. The bulk density is not a reliable parameter for granulated or powdery products, in that even imperceptible perturbations of the test sample can give rise to remarkably different bulk density values. For the characterization of the density of said materials the tapped density is preferably used, which is the limit density obtained after tapping down the material by subjecting a graduated cylinder containing the granulate or powder to strokes, namely by hoisting the cylinder to a fixed height then dropping it for a fixed number of times.

The tapped density is usually determined according to the method described in U.S. Pharmacopoeia, National Formulary, Supplement, USP 23, NF 18, Nov. 15, 1997, pages 3976–3977. Said method is herein incorporated by reference.

The material is passed through a 1 mm (n. 18 mesh) sieve to crush any agglomerates formed during storage. About 100 g (M) of the test material are placed without tapping down in a 250 mL graduated cylinder.

Using a suitable device, the cylinder is hoisted then dropped under the action of its own weight, from a height of 14+2 mm, with a 300 times/minute fall frequency. The volume of the material after a first 500 fall cycle is then measured. After a second 750 fall cycle, the volume of material is measured again, and this is considered the final volume ($V_f$) if it does not differ from the first volume by more than 2%. Otherwise, one or more further 1250 fall cycles are carried out until the final volume does not differ from the previous value by more than 2%. The tapped density, in g/mL, is expressed by the formula: $M/V_f$.

Whereas the known processes do not provide granulates or powders of the above mentioned L(−)-carnitine salts, particularly of L(−)-carnitine acid fumarate, with tapped density values reproducible and suitable for a satisfactory processability in standard devices, the process of the present invention attains said object while overcoming other drawbacks, as it will be further described in details hereinbelow.

The process of the invention for the preparation of a stable, non-hygroscopic L(−)-carnitine salt selected from the group consisting of L(−)-carnitine acid fumarate (1:1) and L(−)-carnitine L(+)-tartrate (2:1), comprises:

(a) mixing at room temperature, in any desired order,
  (1) L(−)-carnitine inner salt;
  (2) fumaric acid or L(+)-tartaric acid, respectively in equimolar amount or in half the equimolar amount to L(−)-carnitine inner salt; and
  (3) 5–9%, preferably 6–8%, by weight of water calculated on the weight of the (1)+(2)+(3) mixture;

(b) heating under stirring the above mixture at a temperature of 100–120° C. to obtain a substantially colourless, transparent molten mass;

(c) cooling the molten mass until complete solidification; and (d) grinding the solidified mass to obtain a granulate or powder having the desired particle size.

In step (a), water, in amount only 5–9%, preferably 6–8%, by weight calculated on the weight of the (1)+(2)+(3) mixture, cannot be considered either "the minimum amount of water necessary to obtain a mixture of semiliquid/pasty consistency "of L(−)-carnitine inner salt and fumaric or L(+)-tartaric acid, according to the teachings of the above mentioned WO 98/38157 (in fact the mixture of step (a) is not in such form), or, even less, a solvent for said reagents. In the process according to the invention, water rather acts as an adjuvant for the subsequent melting step (b) which, due to the presence of water, takes place at a temperature (100–120° C.) lower than the melting points of both the reagents and the final salts. The process of the present invention can therefore be defined as a "humid melting process" also considering the solidification pattern of the liquid (molten) mass of step (c) which solidifies as a glassy solid wherein, in the first solidification period, a number of crystallization seeds can be detected.

In step (c), "cooling" means both simply promoting the cooling of the fluid mass, for example by pouring it onto a cold surface (even at room temperature) and inducing cooling (therefore accelerating it) by the use of suitable ventilation means or moving the fluid mass to a container equipped with a cooling jacket, as it is well known to those skilled in the art.

The "complete solidification" can be the direct result of the above defined cooling (promoted or accelerated) or be induced (and then further accelerated compared with the simple cooling procedure) by adding a crystallization initiator to the still fluid mass. Preferably 1–2% by weight on the weight of the stirred mass of a fine powder of L(−)-carnitine acid fumarate (1:1) or of L(−)-carnitine L(+)-tartrate (2:1) is added, respectively. The addition is preferably carried out when the temperature of the cooling mass is about 60–90° C. operating according to the two different procedures mentioned above, the duration of the solidification step can be suitably varied from about 60 minutes (with no crystallization initiator) to about 1–5 minutes.

The grinding step (d) can be carried out in a single operation or in two sub-steps, (d.1) and (d.2): in (d.1) a first coarse grinding is effect to promote drying of the solidified mass (which takes place very quickly by keeping the resulting granulate at 50–60° C. under vacuum); in (d.2) grinding of the dried product is continued until the desired particle size is achieved.

Operation according to the processes known in art could never provide granulates or powders of L(−)-carnitine acid fumarate having tapped density of at least 0.8 g/mL, therefore the present invention further relates to such granulates or powders as novel products. Preferably, the tapped density thereof is 0.82–0.86 g/mL. Said tapped density values, which are always reproducible when obtained by the process of the invention, are optimum to provide an excellent processability of the relevant granulate or powder.

EXAMPLE 1

Preparation of L(−)-carnitine Acid Fumarate

A mixture of L(−)-carnitine inner salt (28.98 g; 0.18 mols), finely powdered fumaric acid (99%) (21.15 g; 0.18 mols) and 4.30 mL of water (water content in the mixture: about 7.9%), was quickly heated under stirring in a flask, at 110–120° C., until obtaining a liquid, transparent mass in 1–2 minutes. After stopping heating, the liquid was stirred for a further 30 seconds, then poured onto a cold surface (at room temperature).

In a few minutes the liquid solidified into a glassy solid in which crystallization germs appeared in a short time. The mass was left to stand for 40–50 minutes until complete solidification as an opaque, white solid, which could be immediately ground.

The ground product was dried in a static dryer at 50–60° C. under vacuum. This occurred very quickly, considering temperature of the salification reaction which provided a product with a very low water percent content already after grinding. The yield was quantitative.

The title compound was further ground to the desired particle size, occurred as a flowable, non-hygroscopic granulate, which remained unchanged in time without undergoing packing and/or aggregation.

The tapped density of the granulate (determined with the method of U.S. Pharmacopoeia described above) was 0.84 g/mL.

EXAMPLE 2

Preparation of L(−)-carnitine Acid Fumarate (in the presence of a Crystallization Initiator)

The procedure of Example 1 was repeated, except that, after stopping heating, the liquid mass was left to cool at 80° C. and added with about 50 mg of solid, finely powdered L(−)-carnitine acid fumarate, under stirring. The liquid solidified in 1–2 minutes as a crystalline solid, which could be immediately ground (the solidification time was shortened by above 90% compared with the preparation of Ex. 1). The procedure described in Example 1 was then followed. Quantitative yield.

Physico-chemical characteristics of the final compound: the same as those obtained in the preparation of Example 1.

EXAMPLE 3

Preparation of L(−)-carnitine Tartrate (2:1)

The procedure of Example 1 was repeated with a mixture consisting of 32.2 g (0.2 mols) of L(−)-carnitine inner salt, 15.0 g (0.1 mols) of L(+)-tartaric acid and 4.0 mL of water (water content in the mixture: 7.8%). The only difference was that the liquid mass was not completely transparent as in Example 1. Quantitative yield. Tapped density of the granulate: 0.83 g/mL.

The process of the invention has remarkable advantages over the previously known processes.

More specifically, advantages over the prior art processes based on salification in solution and subsequent crystallization are the following:

(a) no organic solvents are used, thus remarkably decreasing production costs, and avoiding any environmental pollution, recycle, fire and explosion problems;

(b) yields are substantially quantitative;

(c) grinding provides the desired particle size of the final product; and (d) the plant sizes can be decreased, the produced amounts being equal.

Advantages over the process described in WO 98/38157 are the following:

(e) use of conventional devices, such as, for the heating step (b), a common reactor equipped with stirrer and heating jacket;

(f) perfect blending of the reagents in a short time;

(g) working with large amounts per batch;

(h) shorter drying steps due to the low water content in the starting mixture;

(i) possibility to carry out the solidification in any desired container; and (j) possibility to vary the solidification time as desired.

One of the most significant advantages provided by the process of the invention compared with any known process is, however, the capability to prepare in a perfectly reproducible way granulates or powders of said L(−)-carnitine salts having tapped density of at least 0.8 g/mL, which, together with a flexible particle size distribution, allows to overcome any processability problems of said materials on standard devices, such as conventional tabletting devices and the like.

This result is particularly important for L(−)-carnitine acid fumarate (1:1) which, when prepared with conventional processes, has inadequate tapped density, varying from 0.4 to 0.6 g/mL depending on the batches, and an uneven particle distribution, thus creating serious, or even insurmountable, problems affecting processing and therefore transformation into end products.

What is claimed is:

1. A process for the preparation of a stable, non-hygroscopic salt of L(−)-carnitine selected from the group consisting of L(−)-carnitine acid fumarate (1:1) and L(−)-carnitine L(+)-tartrate (2:1), comprising:

a) mixing at room temperature, in any desired order, (1) L(−)-carnitine inner salt;

(2) fumaric acid or L(+)-tartaric acid, respectively in equimolar amount or in half the equimolar amount to L(−)-carnitine inner salt; and (3) 5–9%, preferably 6–8%, by weight of water calculated on the weight of the (1)+(2)+(3) mixture;

(b) heating under stirring the above mixture at a temperature of 100–120° C. to obtain a substantially colourless, transparent molten mass;

(c) cooling the molten mass until complete solidification; and (d) grinding the solidified mass to obtain a granulate or powder having the desired particle size.

2. A process as claimed in claim 1, in which in step (c) the cooling mass is added with 1–2% by weight, calculated on the mass weight, of a crystallization initiator consisting of a fine powder of L(−)-carnitine acid fumarate (1:1) or of L(−)-carnitine L(+)-tartrate (2:1), respectively.

3. A process as claimed in claim 2, in which the addition of the crystallization initiator is carried out when the cooling mass has a temperature of 60–90° C.

4. A process according to claim 1, in which the grinding step (d) comprises:

(d.1) a first coarse grinding, optionally under vacuum and at 50–60° C., to promote drying of the solidified mass; and (d.2) a further grinding of the dried product to obtain the granulate or powder of the desired particle size.

5. A granulate or powder substantially comprising L(−)-carnitine acid fumarate (1.1), whose tapped density is at least 0.8 g/mL.

6. A granulate or powder as claimed in claim 5, whose tapped density is 0.82–0.86 g/mL.

* * * * *